United States Patent [19]

Isenberg

[11] Patent Number: 4,702,971
[45] Date of Patent: Oct. 27, 1987

[54] SULFUR TOLERANT COMPOSITE CERMET ELECTRODES FOR SOLID OXIDE ELECTROCHEMICAL CELLS

[75] Inventor: Arnold O. Isenberg, Pittsburgh, Pa.

[73] Assignee: Westinghouse Electric Corp., Pittsburgh, Pa.

[21] Appl. No.: 867,860

[22] Filed: May 28, 1986

[51] Int. Cl.⁴ .............................................. H01M 8/12
[52] U.S. Cl. ........................................ 429/31; 429/41; 429/44; 429/33
[58] Field of Search ............... 42/30, 31, 41, 44, 45, 42/33

[56] References Cited

U.S. PATENT DOCUMENTS

| | | | |
|---|---|---|---|
| 3,573,993 | 4/1971 | Pabst et al. | 429/30 |
| 3,578,502 | 5/1971 | Tannenberger et al. | 429/44 |
| 4,297,419 | 10/1981 | Nickols, Jr. et al. | 429/44 |
| 4,317,866 | 3/1982 | Trocciola et al. | 429/41 |
| 4,490,444 | 12/1984 | Isenberg | 429/31 |
| 4,517,260 | 5/1985 | Mitsuda | 429/41 |
| 4,547,437 | 10/1985 | Isenberg et al. | 429/30 |
| 4,562,124 | 12/1985 | Ruka | 429/30 |
| 4,582,766 | 4/1986 | Isenberg et al. | 429/30 |
| 4,596,750 | 6/1986 | Ruka et al. | 429/16 |
| 4,597,170 | 7/1986 | Isenberg | 29/623.5 |
| 4,598,028 | 7/1986 | Rossing et al. | 429/30 |

Primary Examiner—John F. Niebling
Assistant Examiner—Steven P. Marquis
Attorney, Agent, or Firm—Daniel P. Cillo

[57] ABSTRACT

An electrochemical apparatus is made containing an exterior electrode bonded to the exterior of a tubular, solid, oxygen ion conducting electrolyte where the electrolyte is also in contact with an interior electrode, said exterior electrode comprising particles of an electronic conductor contacting the electrolyte, where a ceramic metal oxide coating partially surrounds the particles and is bonded to the electrolyte, and where a coating of an ionic-electronic conductive material is attached to the ceramic metal oxide coating and to the exposed portions of the particles.

23 Claims, 6 Drawing Figures

SULFUR TOLERANT COMPOSITE CERMET ELECTRODES FOR SOLID OXIDE ELECTROCHEMICAL CELLS

GOVERNMENT CONTRACT CLAUSE

The Government of the United States of America has rights in this invention pursuant to Contract No. DE-AC-0280-ET-17089, awarded by the U.S. Department of Energy.

BACKGROUND OF THE INVENTION

The use of nickel-zirconia cermet anodes for solid oxide electrolyte fuel cells is well known in the art, and taught, for example, by A. O. Isenberg in U.S. Pat. No. 4,490,444. This fuel electrode or anode must be compatible in chemical, electrical, and physical-mechanical characteristics such as thermal expansion, to the solid oxide electrolyte to which it is attached. A. O. Isenberg, in U.S. Pat. No. 4,597,170 solved bonding and thermal expansion properties between the anode and solid oxide electrolyte, by use of a skeletal embedding growth, of for example, primarily ionic conducting zirconia doped with minor amounts of yttria, covering lower portions a porous nickel powder layer comprising the porous cermet anode.

This anchoring of the anode nickel particles to the solid oxide electrolyte was accomplished by a modified chemical vapor deposition process, usually providing a dense deposit. While this process provided well bonded anodes, having good mechanical strength and thermal expansion compatibility, gas diffusion overvoltages were observed during operation, lowering overall cell performance. Additionally, these anodes were not found to be particularly tolerant of sulfur contaminants.

In order to reduce gas diffusion overvoltages A. O. Isenberg et al., in U.S. Pat. No. 4,582,766, taught oxidizing the nickel particles in the cermet electrode to form a metal oxide layer between the metal particles and the electrolyte, while additionally providing porosity in the embedding skeletal member, and then reducing the metal oxide layer to form a porous metal layer between the metal electrode particles and the electrolyte; all allowing greater electrochemical activity. Such structures were still not found to be particularly sulfur tolerant, however, and provide a limited number of electrochemical sites. What is needed is a sulfur tolerant anode structure having low diffusion overvoltages coupled with long periods of acceptable performance.

SUMMARY OF THE INVENTION

The above problems have been solved and the above needs met by providing an electrode, bonded to a solid oxygen conducting electrolyte, containing particles of an electronic conductor partly embedded in a skeletal member of a ceramic metal oxide, where the surface of the particles and skeleton are contacted, preferably covered completely, with a separate, porous, gas permeable oxygen-ionic-electronic conductor material coating. This coating is sinter, or diffusion attached, electronically conductive, and can contain, preferably, doped or undoped ceria, doped or undoped urania, or their mixtures. Ceria based outer coatings are preferably doped with zirconia, thoria or lanthanide oxides. Urania based coatings are also doped with these oxides. These oxides are known to be compatible with yttria stabilized zirconia electrolyte, and interdiffusion, if present at high temperatures, is not detrimental to cell performance or life.

Ceria based and urania based oxides, besides being oxygen ionic conductors, exhibit considerable electronic conduction as compared to zirconia, especially at oxygen activities at which fuel cell metal electrodes are used. This fact increases considerably the active surface area of the electrode for electrochemical redox reactions. Adsorption of sulfur species on active sites, which is the reason for low sulfur tolerance of the cermet electrodes, is therefore greatly reduced in severity during electrode operation. After applying the oxide coating, a thermal treatment, at from about 500° C. to about 1400° C. in an atmosphere that prevents cermet oxidation, advantageously allows elements from the ceria based or urania based oxide outer coating to diffuse into the skeleton structure, and introduce increased electronic conduction to the skeleton.

The resulting coated electrodes have increased numbers of active electrode sites, are mechanically strong provide low diffusion overvoltage, long periods of outstanding performance, and, very importantly, are more tolerant to fuel contaminants such as sulfur and other sulfur species.

BRIEF DESCRIPTION OF THE DRAWINGS

For a better understanding of the invention, reference may be made to the preferred embodiments exemplary of the invention shown in the accompanying drawings, in which.

DESCRIPTION OF THE PREFERRED EMBODIMENTS

Figure 1:
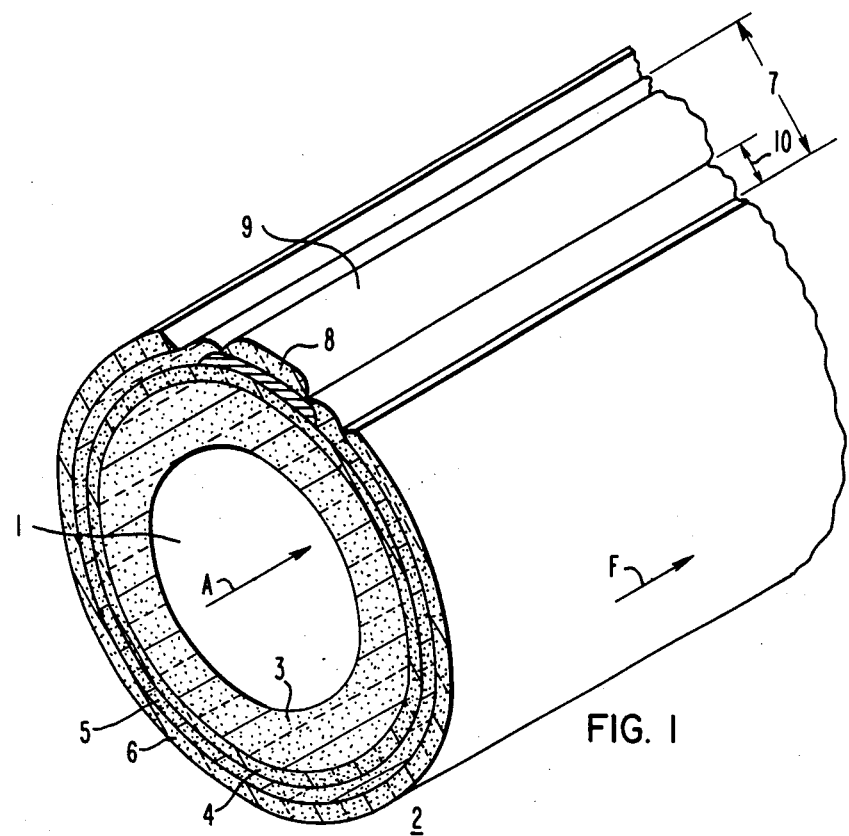
FIG. 1 is an isometric view in section of one embodiment of a tubular solid oxide fuel cell according to this invention.

Referring now to the Drawings, FIG. 1 shows air or oxygen, A, flowing through the center 1 of the tubular fuel cell 2. The air (oxygen) permeates through porous support tube 3 to air electrode 4 where oxygen is converted to oxygen ions. The oxygen ions are conducted through electrolyte 5 to fuel electrode anode 6, where they react with fuel, F, such as $H_2$, CO, $CH_4$, etc., to generate electricity. As can be seen, the fuel electrode in this configuration is an exterior electrode, where the electrolyte 5 is in tubular form and in contact with an interior electrode 4.

Also shown in FIG. 1 are longitudinal space 7 containing an interconnection 8 for making electrical connections from the underlying air electrode to the fuel electrode 6 of an adjacent cell tube (not shown) and an electronically insulating gap 10. A metal or fuel electrode type of material 9 is coated over interconnection 8. A detailed description of the general operation of the solid oxide fuel cell, along with appropriate description of useful support, air electrode, and interconnection materials, can be found in U.S. Pat. No. 4,490,444, assigned to the assignee of this invention.

Figure 2:
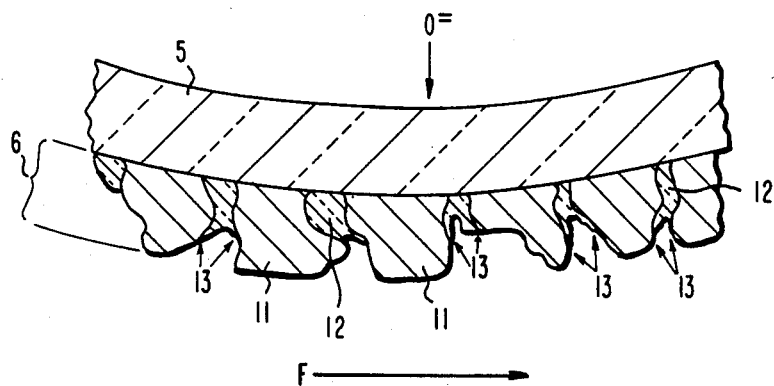
FIG. 2 is a schematic end view in section showing a fuel electrode having metal particles partly embedded in an oxide skeleton structure, all disposed on top of an electrolyte.

FIG. 2 is a much enlarged and detailed schematic illustration of the fuel electrode structure 6, where only a skeleton embedding structure is applied to metallic particles comprising the anode. In FIG. 2, an electrolyte 5 is contacted with particles 11 of a metallic conductor which forms the fuel electrode. A ceramic skeletal coating 12 covers small portions of the particles 11 and binds them to the electrolyte 5.

The cell and electrolyte 5 can have a variety of shapes but the preferred shape is a tubular, as that configuration is the most useful for solid oxide electrochemical cells. The electrolyte material 5 is typically an oxide having a fluorite structure or a mixed oxide in the perovskite family, but other simple oxides, mixed oxides, or mixtures of simple and mixed oxides can be used. The preferred electrolyte material is stabilized zirconia, a readily available commercial material. The zirconia may be stabilized, i.e., doped, with a number of elements, as is well known in the art, but rare earth element stabilized zirconia, specifically yttris stabilized zirconia, is preferred as it has excellent oxygen ion mobility. A preferred composition is $(ZrO_2)_{0.90}(Y_2O_3)_{0.10}$ as that material works well in solid oxide electrochemical cells. Other mixed oxides can be used including yttrium doped thorium oxide. The method of this invention is applicable to oxide layers which transfer oxygen in any form including monoatomic oxygen as well as ionic oxygen.

A preferred fuel electrode thickness is about 50 microns to about 200 microns, though the thickness may be adjusted to the desired resistance of the cell. An electronic conductor can be used in particulate form in the fuel electrode 6. Metals are preferred as they are more conductive and reduce cell resistance, but oxides can also be used. Metals are preferred to metal oxides for a fuel cell because the atmosphere is generally reducing.

Metals that can be used as the electronic conductor particles 11 include platinum, gold, silver, copper, iron, nickel, cobalt and alloys and mixtures thereof. Metal oxides that can be used include chromic oxide, lanthanum chromite, and lanthanum manganite. The preferred materials are nickel, cobalt, alloys thereof and mixtures thereof, as these metals are less expensive, more stable, more sulfur resistant, and have an acceptable oxidation potential. The particles 11, which are preferably from about 1 micron to about 5 microns diameter, may be applied to contact the electrolyte as a powder layer in many different ways, including slurry dipping and spraying. Another method of application is a tape transfer technique, which is useful because of ease of mass fabrication, registering of dimensions, and uniformity in thickness and porosity.

The material which binds the conductor particles to the electrolyte and provides a skeleton partly embedding the conductor particles can be applied by vapor deposition and formed from two reactants. The first reactant can be water vapor, carbon dioxide or oxygen itself, and the second reactant can be a metal halide, preferably zirconium tetrachloride, plus the halide of a stabilizing element, such as yttrium chloride. The skeletal binding material 12 is preferably selected to be the same material as the electrolyte (or the same material modified by doping) so that a good bond forms between the binding material 12 and the electrolyte 5 and there is a good thermal match between the two materials. Also, doping with, for example, transition metal elements, can provide a binding material which improves electrode performance. The preferred binding material is yttria stabilized zirconia although a wide variety of ceramic metal oxides that are compatible with the electrolyte can be used.

The skeleton structure 12, when deposited by vapor deposition, has been found to grow around the metal particles 11. In order to form the particle embedded skeleton structure, a coating of the metal powder layer is first applied to one surface of the solid oxide electrolyte. Then, an oxygen gas is applied to the other surface of the electrolyte while a metal halide vapor is applied to the metal particle side. The electrolyte is heated to a temperature sufficient to induce oxygen to diffuse through the electrolyte and react with the halide vapor causing a skeletal coating to grow partly around the metal particles, as described in greater detail in U.S. Pat. No. 4,597,170, herein incorporated by reference.

Electrochemically active sites in solid state electrochemical cells are where the reactant, electrolyte and electrode interface. In the case of FIG. 2, these electrochemically active sites 13 are where the fuel gas, F, is capable of combining with oxygen ions and where electron transfers can take place to generate an electric current. As can be seen, by using an embedding skeleton alone, the number of active areas 13 is rather limited. Due to the fact that these electrodes have a relatively small number of active sites, the cell can be rapidly affected by contaminants that can block these sites. Sulfur and sulfur species, for example, are absorbed stronger on these sites than carbon monoxide and hydrogen and therefore reduce overall cell performance.

Figure 3:
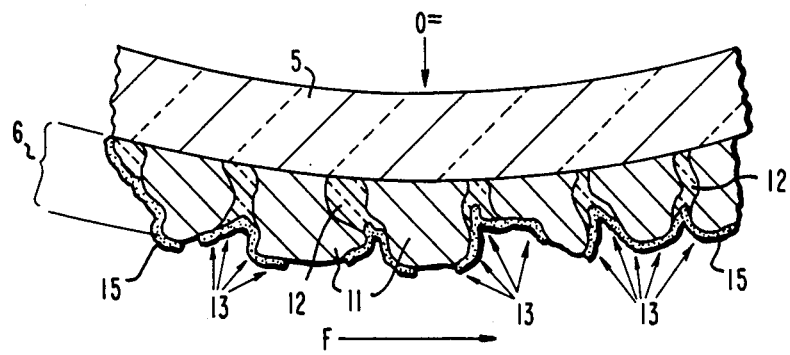
FIG. 3 is a schematic end view in section of the electrode of this invention having an ionic electronic conductor outer coating over both the metal particles and the partly embedding skeleton structure.

FIG. 3 shows the electrode structure of this invention, where the electrode 6 is bonded to a solid, oxygen ion-conducting electrolyte 5. The electrode comprises particles of electronic conductor 11 partly embedded in a skeletal member of a ceramic metal oxide 12. The particles and skeleton are covered, preferably completely, with an ionic-electronic conductor coating 15. This coating layer can be dense or porous, depending on the technique of application. The coating can be applied by any means, although simple impregnation from an aqueous solution, a solvent solution, such as an alcohol solution, or a fine suspension, is preferred.

Useful ceramic oxides for the coating 15 are those that are both ionic and electronic conductive. Preferred ceramic oxides for the coating 15 are doped or undoped ceria and doped or undoped urania. By the term "doped" is meant inclusion of from about 1 mol% to about 70 mol% of a doping element, which either causes increased oxygen ion conduction or electronic conduction or both. High doping may result if a mixture of dopants are used. Dopants for both ceria and urania can include oxides of the rare earth metals, i.e. elements 57 to 71: La, Ce, Pr, Nd, Pm, Eu, Gd, Tb, Dy, Ho, Er, Tm, Yb and Lu, as well as zirconium, yttrium, scandium and thorium, and their mixtures. The preferred dopants are zirconia, thoria and lanthana.

The outer coating 15 is capable of free expansion and contraction during fuel cell heat cycling. The coatings are thin and may be discontinuous as shown in FIG. 3. Coating cracking or partial flaking is not deleterious to performance since most flaked particles would be trapped in the porous electrode structure and become active again in a new position. The electrode active site triple point sites 13 are spread over the surface of the outer coating 15, as shown in FIG. 3. Here, the ionic-electronic conductive coating 15 is capable of transporting $O^=$ ions, from the essentially only ionic conductive skeleton 12 to contact fuel. Thus, the active sites are not limited to the juncture of the ionic conductive skeleton 12 and the metallic particle 11, but are vastly expanded because the coating layer conducts $O^=$ ions, conducts electrons, and in most cases is porous to fuel gas. The thickness of coating 15 is from about 0.5 micron to about 20 microns and is preferably continuously attached throughout the entire surface of the porous cermet electrode. Preferably, after application of the ceramic oxide coating 15, it is subjected to a heat treatment at temperatures from about 500° C. to about 1400° C. to form the oxide coatings or to diffuse elements from the coating into the skeleton, introducing increased electronic conduction into the skeleton, thus making the skeleton 12 more of an active part of the electrode.

In one method of coating, the metal particle embedded electrode is impregnated with a metal salt solution, that, when heated up to operating temperatures of the solid oxide cells, i.e., over about 500° C., decomposes or reacts to form the desired mixed oxide coating. For example, an aqueous mixed solution of lanthanum nitrate and cerium nitrate can be used. When the solution dries and the salt is heated up it will decompose to a mixed oxide of lanthanum-doped cerium oxide. This oxide will coat the surface of the porous cermet electrode. This coating is polycrystalline and is relatively weakly attached. It is protected, however, by the porous and rigid overall electrode structure.

As a result of this coating, the active electrode surface area is greatly enlarged. Thermal cycling of electrodes does not lead to electrode deterioration, since the coating can freely expand. An electrode of this kind could also be prepared by impregnation of electrodes with fine oxide suspensions, which requires a very fine particle size of the oxide. Other solution of salts can be used advantageously, for instance, a methanol solution of the hexahydrates of cerium nitrate and lanthanum nitrate is preferred because of its superior wetting behavior.

While the electrodes of this invention are primarily useful in solid oxide fuel cells, they can also be used as electrodes for solid state electrolyzers and gas sensors.

EXAMPLE

A tubular cell closed at one end was prepared. It was 400 mm long and 13 mm in diameter, consisting of a 2 mm thick porous support tube of calcia stabilized zirconia, a 1 mm thick 40% porous air electrode of doped lanthanum manganite on top of the support tube, and a 50 micron thick electrolyte of yttria stabilized zirconia $(ZrO_2)_{0.90}(Y_2O_3)_{0.10}$ on the air electrode. A 100 micron thick layer of about five micron diameter nickel powder was deposited over the electrolyte by means of slurry dipping. The nickel layer was about 50% porous. A ceramic skeleton of yttria stabilized zirconia was deposited around the nickel powder layer to mechanically attach it to the electrolyte, according to a process described in copending U.S. patent application Ser. No. 716,865, incorporated herein by reference.

The ceramic skeleton was about 1 to 5 microns thick and partly embedded the nickel powder layer extending throughout this layer from the surface of the electrolyte, but being thicker near the electrolyte. The finished electrode thus constituted a cermet consisting of nickel and reinforcing zirconia ceramic.

The porous cermet electrode was then impregnated with a room-temperature, saturated solution of cerium nitrate and lanthanum nitrate, which was prepared by dissolving the hexahydrates of these salts in methanol. Methanol is the preferred solvent because of good wetting characteristics but other solvents such as water and other alcohols can also be used. The solution was applied by brushing. The impregnated electrode was then dried in a hood at room temperature.

The impregnated salts were thermally decomposed to a mixed oxide during a heat-up procedure for testing the cell. The heating rate was about 1 hour, from room temperature to 1000° C. The resulting impregnated oxide covering was a lanthanum-doped cerium oxide $(CeO_2)_{0.8}(La_2O_3)_{0.2}$. The tube had an active electrode area of about 110 $cm^2$, which was impregnated with 2.8 $mg/cm^2$ of the lanthanum doped cerium oxide solids. Microscopic examination of electrodes after testing showed that the oxide impregnation was embedded in the voids of the porous nickel-zirconia cermet electrode. The impregnated oxide weight varies with electrode porosity and thickness and can be as low as 0.5 $mg/cm^2$ or as high as 10 $mg/cm^2$. Due to the fact that the impregnated finely divided oxide covering was a mixed electronic-oxygen/ionic conductor, it is an integrated part of the electrode and provides additional active electrode area over that of an unimpregnated electrode. Therefore, higher current densities can be achieved whether the cell operates as a fuel cell or as an electrolysis cell.

Figure 4:
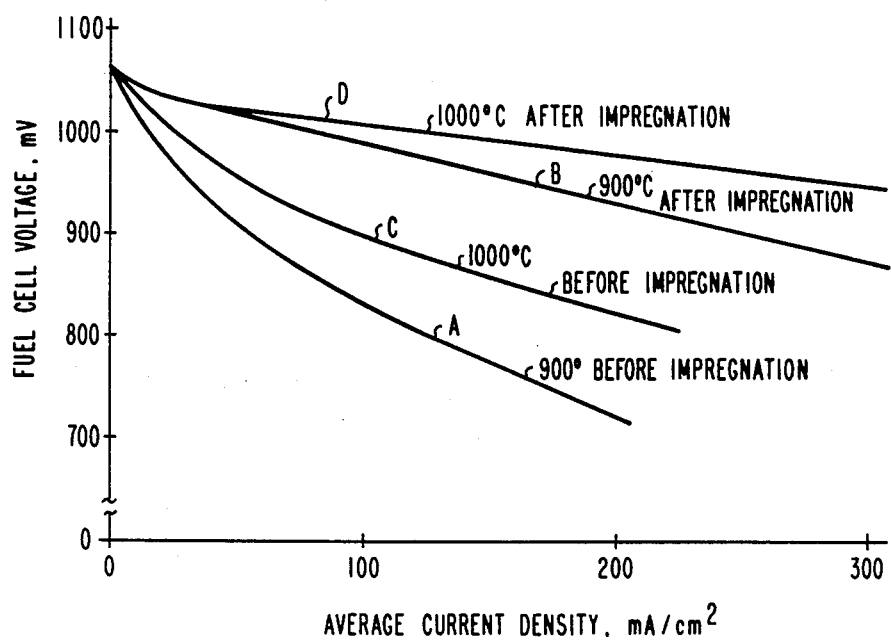
FIG. 4 is a graph of fuel cell voltage vs. average current density, showing improvement of fuel cells after anode impregnation with lanthanum-doped ceria, as described in the Example.
Figure 5:
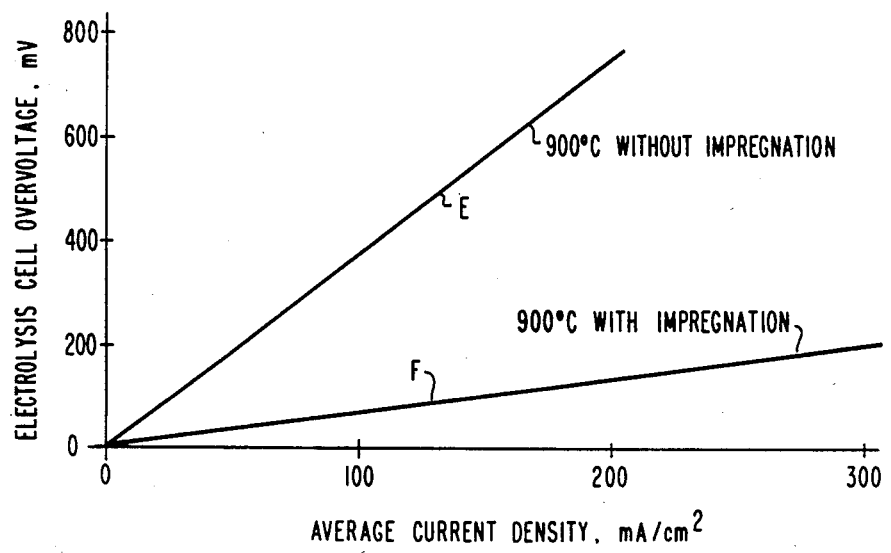
FIG. 5 is a graph of electrolysis cell overvoltage vs. average current density, showing overvoltage reduction of electrolysis cells after anode impregnation with lanthanum-doped ceria, as described in the Example.

FIG. 4 of the drawings shows behavior of a cell at 900° C., before impregnation (line A) and after impregnation (line B), and at 1000° C., before impregnation (line C) and after impregnation (line D), when the cell operated as a fuel cell. Lines B and D correspond to the fuel cell construction of this invention and show very much improved results over lines A and C. The VI-characteristics were achieved with hydrogen/3% $H_2O$ as fuel (less than 10% fuel utilization) and air. This test cell, utilizing the same cell geometry but a shorter section, was also tested in the electrolysis mode, and the performance is shown in FIG. 5, which demonstrates that the cell performance is also greatly improved when the cell operates an an electrolyzer of $CO_2$, $H_2O$ or mixtures of these gases. FIG. 5 shows the IR-free overvoltage of the electrolyzer cell characteristic after 24 hours at 900° C. when operated without impregnation (line E), and the improvement observed with impregnation (line F). The cathode gas consisted of a cell inlet gas mixture of 77% $CO_2$ and 23% $H_2$. The gas composition shifts according to the water gas reaction: $CO_2 + H_2 \rightleftharpoons H_2O + CO$. The cell, therefore, electrolyzes steam as well as carbon dioxide. The greatly reduced electrode overvoltage of line F attests to the uniqueness of this composite cermet electrode as an anode (in fuel cells) and as a cathode (in electrolyzers).

Figure 6:
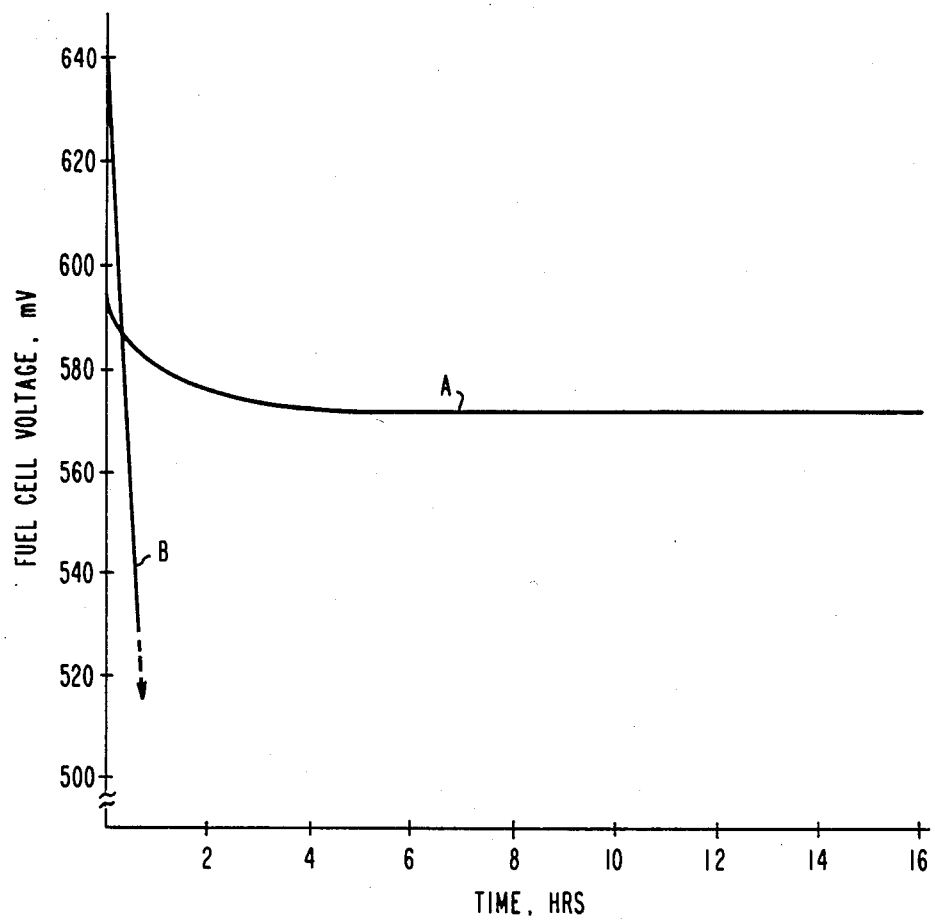
FIG. 6 is a graph of fuel cell voltage vs. time, showing vastly improved sulfur tolerance of lanthanum-doped ceria electrodes, as described in the Example.

A major and unexpected result of this new electrode structure is the fact that it exhibits sulfur stability during operation. This improvement is demonstrated in FIG. 6, where the cell voltage curve of a fuel electrode of a solid oxide fuel cell made as described in the Example, of 110 cm$^2$ active surface area impregnated with 2.8 mg/cm$^2$ of lanthanum-doped ceria $(CeO_2)_{0.8}(La_2O_3)_{0.2}$ is shown as line A. The cell operated at 1000° C. and at a constant fuel utilization of 85%, using a fuel of 67% $H_2$, 22% CO and 11% $H_2O$. The average current density was 250 mA/cm$^2$. Fifty ppm of hydrogen sulfide was added to the fuel, which led to a 4.7 percent performance loss. A similar size cell B of identical construction but without the impregnation was exposed to the same conditions, and an unacceptable performance loss was recorded in a very short time (line B), which increased continuously to an unacceptable level, while the electrode according to this invention stabilized after a short time (line A).

I claim:

1. An electrode bonded to a solid, ion conducting electrolyte, said electrode comprising:
   (A) particles of an electronic conductor,
   (B) an ion conducting ceramic metal oxide partially surrounding said particles, and bonded to the electrolyte, and
   (C) an ionic-electronic conductive coating on said ion conducting ceramic metal oxide and exposed portions of the particles.

2. The electrode of claim 1, where the particles are metal particles, and the ionic-electronic conductive material comprises an oxide selected from the group consisting of ceria, doped ceria, urania, doped urania, and mixtures thereof.

3. The electrode of claim 1, where the electrolyte and the ion conducting ceramic metal oxide comprises stabilized zirconia.

4. The electrode of claim 1 where the ceramic metal oxide is an essentially only ionic conductive skeleton structure partially surrounding the particles, the ionic-electronic conductive material consists essentially of ceria, urania, doped ceria, doped urania and mixtures thereof where the dopant for ceria is selected from the group consisting of zirconia and thoria, the electrolyte and the ion conducting ceramic metal oxide consist essentially of stabilized zirconia, and where the ionic-electronic conductive material is effective to provide electrochemically active sites over its entire surface and sulfur stability while operating in the presence of sulfur and sulfur species.

5. An electrode bonded to a solid, oxygen ion conducting electrolyte, said electrode comprising particles of an electronic conductor partly embedded in a skeletal member of an ion conducting ceramic metal oxide, where exposed surfaces of the particles and ion conducting skeletal member are coated with ionic-electronic conductive material.

6. The electrode of claim 5, bonded to an electrolyte comprising stabilized zirconia, and where the skeletal member comprises stabilized zirconia.

7. The electrode of claim 5, being an exterior electrode where the electrolyte is in tubular form and the electrolyte is also in contact with an interior electrode.

8. The electrode of claim 7, where the electrolyte and skeletal member each comprise yttria doped zirconia and the outer ionic-electronic conductive material comprises an oxide selected from the group consisting of ceria, doped ceria, urania, doped urania, and mixtures thereof.

9. The electrode of claim 5, wherein the particles are from about 1 micron to about 5 microns in size and are a metal selected from the group consisting of platinum, nickel, cobalt, gold, copper, iron, alloys thereof and mixtures thereof.

10. The electrode of claim 5, where the ionic-electronic material is capable of expanding and contracting independent of the other components of the electrode.

11. The electrode of claim 5, where the ionic-electronic conductive material has a thickness of from about 0.5 micron to about 20 microns and is continuous over the entire surface of the electrode.

12. The electrode of claim 5, where the ionic-electronic conductive material comprises an oxide selected from the group consisting of ceria, doped ceria, urania, doped urania, and mixtures thereof.

13. The electrode of claim 5, where the ionic-electronic conductive material comprises an oxide selected from the group of doped ceria, doped urania, and mixtures thereof and the dopant is an oxide selected from the group consisting of zirconium, yttrium, scandium, thorium, rare earth mettals, and mixtures thereof.

14. The electrode of claim 5 where the ionic-electronic conductive material is effective to provide electrochemically active sites over its entire surface, and sulfur stability while operating in the presence of sulfur and sulfur species.

15. The electrode of claim 5, where the electrolyte and skeletal member each comprise yttria doped zirconia.

16. The electrode of claim 5, where the ceramic metal oxide is essentially only ionic conductive, the ionic-electronic conductive material consists essentially of ceria, urania, doped ceria, doped urania and mixtures thereof where the dopant for ceria is selected from the group consisting of zirconia and thoria, and the electrolyte and the ion conducting ceramic metal oxide consist essentially of stabilized zirconia.

17. An exterior electrode bonded to the exterior of a tubular, solid, oxygen ion conducting electrolyte, where the electrolyte is also in contact with an interior electrode, said exterior electrode comprising particles of an electronic conductor partly embedded in a skeletal structure of dense, essentially only ionic conductive ceramic metal oxide, where the electrolyte and skeletal structure comprise stabilized zirconia, and where the particles and skeletal structure are contacted by a separate, ionic-electronic conductive coating which consists essentially of an oxide selected from the group consisting of ceria, doped ceria, urania, doped urania and mixtures thereof.

18. The exterior electrode of claim 17, where the ionic-electronic conductive outer coating oxide is doped with from about 1 mol% to about 70 mol% of an oxide selected from the group consisting of zirconium, yttrium, scandium, thorium, rare earth metals, and mixtures thereof, and where said coating is capable of expanding and contracting independent of the other components of the electrode.

19. The exterior electrode of claim 17, where the ionic-electronic conductive coating is effective to provide electrochemically active sites over its entire surface and sulfur stability while operating in the presence of sulfur and sulfur species, and the exterior electrode, electrolyte, and interior electrode are capable of functioning as a fuel cell or as an electrolysis cell.

20. The exterior electrode of claim 17, where the ionic-electronic conductive material consists essentially of ceria, urania, doped ceria, doped urania and mixtures thereof where the dopant for ceria is selected from the group consisting of zirconia and thoria.

21. A tubular electrochemical cell containing an exterior electrode bonded to the exterior of a tubular, solid, oxygen ion conducting electrolyte, where the electrolyte is also in contact with an interior electrode, said exterior electrode comprising particles of an electronic conductor partly embedded in a skeletal structure of a dense, essentially only ionic conductive ceramic metal oxide, where the electrolyte and skeletal structure comprise stabilized zirconia, and where the particles and skeletal structure are contacted by a separate, ionic-electronic conductive coating which consists essentially of an oxide selected from the group consisting of doped ceria, doped urania, and mixtures thereof.

22. The tubular cell of claim 21, where the conductive outer coating oxide is doped with from about 1 mol% to about 70 mol% of an oxide selected from the group zirconium, yttrium, scandium, thorium, rare earth metals, and mixtures thereof, where said outer coating is capable of expanding and contracting independent of the other components, and where said cell is capable of operating as a fuel cell or an an electrolysis cell.

23. The tubular cell of claim 21 where the ionic-electronic conductive material consists essentially of ceria, urania, doped ceria, doped urania and mixtures thereof where the dopant for ceria is selected from the group consisting of zirconia and thoria, and where the ionic-electronic conductive material is effective to provide electrochemically active sites over its entire surface, and sulfur stability while operating in the presence of sulfur and sulfur species.

* * * * *